(12) United States Patent
Farrand et al.

(10) Patent No.: US 6,183,822 B1
(45) Date of Patent: Feb. 6, 2001

(54) POLYMERIZABLE MESOGENIC FLUOROPHENYLENES

(75) Inventors: Louise Diane Farrand, Manchester; Gabrielle Frances Egan, Dorset, both of (GB)

(73) Assignee: Merck Patent Gesellschaft mit beschrankter Haftung (DE)

( * ) Notice: Under 35 U.S.C. 154(b), the term of this patent shall be extended for 0 days.

(21) Appl. No.: 09/353,626

(22) Filed: Jul. 15, 1999

(30) Foreign Application Priority Data

Jul. 15, 1998 (EP) ................................. 98 113 151

(51) Int. Cl.$^7$ ........................ C09K 19/30; C09K 19/38; C07C 25/13; C07C 25/24; C07C 69/653; G02F 1/137

(52) U.S. Cl. .................... 428/1.1; 428/1.55; 252/299.63; 252/299.67; 570/128; 570/131; 570/133; 349/2; 560/65

(58) Field of Search .................. 252/299.01, 299.66, 252/299.67, 299.63, 582; 428/1.1, 1.55; 570/125, 128, 131, 133; 349/2, 194, 123, 117, 106; 359/3; 424/401; 560/65

(56) References Cited

U.S. PATENT DOCUMENTS

| | | | | |
|---|---|---|---|---|
| 5,645,760 | * | 7/1997 | Yanada et al. | 252/299.66 |
| 5,723,066 | * | 3/1998 | Coates et al. | 252/299.01 |
| 5,746,938 | * | 5/1998 | Coates et al. | 252/299.01 |
| 5,872,665 | * | 2/1999 | Coates et al. | 252/299.01 |

FOREIGN PATENT DOCUMENTS 7-258141 * 10/1995 (JP).

* cited by examiner

Primary Examiner—Shean C. Wu
(74) Attorney, Agent, or Firm—Millen, White, Zelano & Branigan, P.C.

(57) ABSTRACT

The invention relates to polymerizable fluorophenylenes of formula I

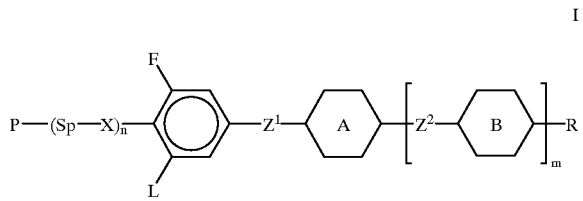

wherein P, Sp, X, n, L, $Z^1$, $Z^2$, A, B, m and R have the meaning of claim 1, to a polymerizable liquid crystalline composition comprising at least one polymerizable mesogenic fluorophenylene of formula I, to the use of the inventive mesogenic fluorophenylenes and compositions comprising them for the preparation of linear or crosslinked liquid crystalline polymers, and to the use of inventive compounds, compositions and polymers in liquid crystal displays, polarizers, compensators, alignment layers, color filters or holographic elements, adhesives, synthetic resins with anisotropic mechanical properties, cosmetics, diagnostics, liquid crystal pigments, for decorative and security applications, in nonlinear optics, optical information storage or as chiral dopants.

16 Claims, No Drawings

POLYMERIZABLE MESOGENIC FLUOROPHENYLENES

SUMMARY OF THE INVENTION

The invention relates to polymerizable mesogenic fluorophenylenes of formula I

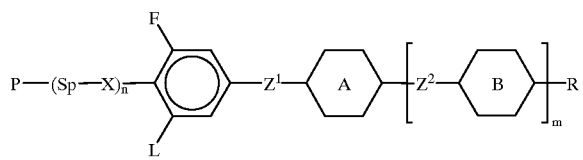

wherein P, Sp, X, n, L, $Z^1$, $Z^2$, A, B, m and R are defined below.

The invention also relates to a polymerizable liquid crystalline composition comprising at least one polymerizable mesogenic compound of formula I, and to the use of the inventive mesogenic compounds and compositions for the preparation of linear or crosslinked liquid crystalline polymers, in particular for the preparation of oriented linear or crosslinked liquid crystalline polymer films.

The invention further relates to the use of inventive compounds, compositions and polymers in liquid crystal displays, such as STN, TN, AMD-TN, temperature compensation, guest-host, phase change, reflective or surface stabilized or polymer stabilized cholesteric texture (SSCT, PSCT) displays, in active and passive optical elements like polarizers, compensators, alignment layers, color filters or holographic elements, in adhesives, synthetic resins with anisotropic mechanical properties, cosmetics, diagnostics, liquid crystal pigments, for decorative and security applications, in nonlinear optics, optical information storage or as chiral dopants.

Polymerizable mesogenic compounds, which are also known as reactive mesogenic compounds, have been described in prior art for various purposes. For example, they can be polymerized in situ whilst being macroscopically oriented in the liquid crystalline state to give anisotropic linear or crosslinked polymers or polymer films with uniform orientation of high quality. These films can be used for example as optical elements like broad band cholesteric polarizers (see EP 0 606 940) or polarization filters (EP 0 397 263).

The WO 93/22397, DE 195 04 224 and WO 97/34862 for example disclose polymerizable mesogenic compounds with mesogenic cores of various structures.

The polymerizable mesogenic compounds described in prior art, however, often exhibit liquid crystalline phases only in a small temperature range or do not show mesophase behavior at all. Another drawback for specific applications is that prior art compounds often exhibit high values of the birefringence.

In particular where polymerizable mesogenic compounds are used in optical phase retardation, compensation or alignment layers or films for liquid crystal displays, it is desirable to have available materials of which the optical properties, such as the birefringence, phase retardation (i.e. the product of birefringence and layer thickness) and dispersion (i.e. the wavelength dependence of the birefringence) are adapted to those of the liquid crystal mixture in the display cell, so that optimum compensation can be achieved.

Thus, there is still a demand for polymerizable mesogenic compounds with a broad liquid crystalline phase and a low value of birefringence.

Furthermore, regarding the broad range of applications for polymerizable mesogenic compounds it is desirable for the expert to have available further compounds of this type which are easy to synthesize and fulfill the various requirements as described above.

It was an aim of the invention to provide new polymerizable mesogenic compounds with advantageous properties, thus extending the pool of reactive liquid crystal compounds available to the expert. Other aims of the present invention are immediately evident to the person skilled in the art from the following detailed description.

It was now found that these aims can be achieved by providing polymerizable mesogenic fluorophenylenes of formula I.

The terms polymerizable mesogenic compound as used in the foregoing and the following comprise compounds with a rod-shaped, board-shaped or disk-shaped mesogenic group, i.e. a group with the ability to induce mesophase behavior in a compound comprising said group. These compounds do not necessarily have to exhibit mesophase behavior by themselves. It is also possible that these compounds show mesophase behavior only in mixtures with other compounds or when the polymerizable mesogenic compounds or the mixtures comprising them are polymerized.

Thus, one object of the invention are polymerizable mesogenic fluorophenylenes of formula I

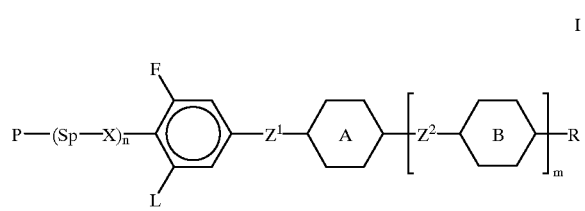

wherein
is $CH_2$=CW—COO—, WCH=CH—O—,

or $CH_2$=CH-Phenyl-(O)$_k$— with W being H, $CH_3$ or Cl and k being 0 or 1,

Sp is a spacer group having 1 to 25 C atoms,

X is —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO—, —OCO—CH=CH—, —C≡C—, or a single bond, n is 0 or 1, L is H or F, $Z^1$ and $Z^2$ are in each case independently —COO—, —OCO—, —CH$_2$CH$_2$—, —OCH$_2$—, —CH$_2$O—, —OCH$_2$—O— or a single bond, A and B are each independently

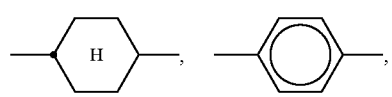

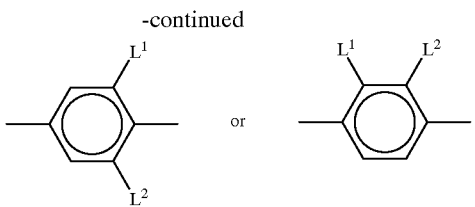

$L^1$ and $L^2$ are H or F, m is 0, 1 or 2, and

R is H, CN, halogen or a straight-chain or branched alkyl radical with up to 25 C atoms which may be unsubstituted, mono- or polysubstituted by halogen or CN, it being also possible for one or more non-adjacent $CH_2$ groups to be replaced, in each case independently from one another, by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another, or alternatively R is P—(Sp—X)$_n$—.

Another object of the present invention is a polymerizable liquid crystalline composition comprising at least two polymerizable compounds, at least one of which is a compound of formula I.

Another object of the present invention is the use of compounds of formula I and compositions comprising them for the preparation of linear or crosslinked liquid crystalline polymers, in particular for the preparation of oriented linear or crosslinked liquid crystal polymer films.

A further object of the invention is a linear or crosslinked polymer that is obtainable by polymerization of one or more compounds of formula I or by polymerization of a composition comprising at least one polymerizable mesogenic compound of formula I and optionally further comprising one or more other polymerizable or non-polymerizable mesogenic or non-mesogenic compounds.

Particularly preferably the inventive polymerizable mesogenic fluorophenylenes are selected of the following formulae

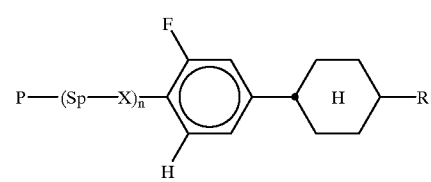

Ia

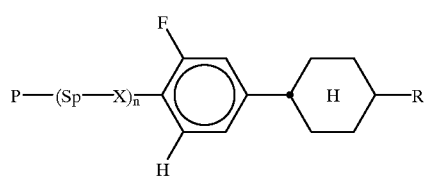

Ib

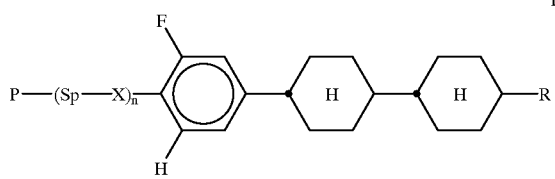

Ic

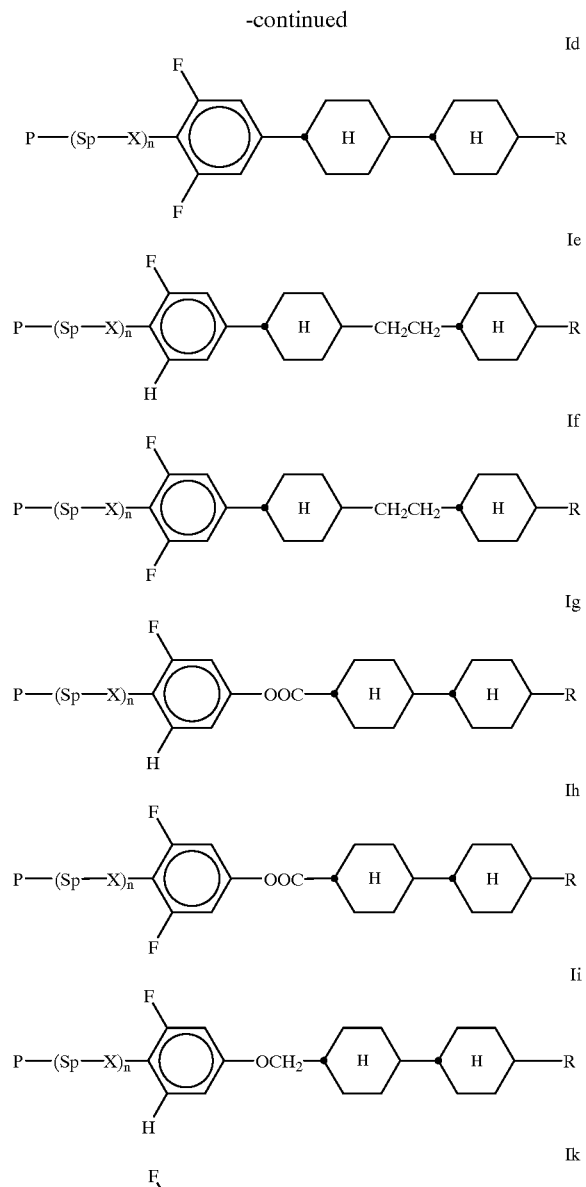

wherein P, Sp, X, n and R have the meanings of formula I.

In particular preferred are compounds of formulae Ic, Id, Ie and If.

Further preferred are compounds wherein L is F, and compounds wherein m is 1 or 2 and $Z^1$ and $Z^2$ are a single bond, R has one of the meanings given for P—(S—X)$_n$—, X is —O—, —CO—, —COO—, —OCO—, —$CH_2$O— or —CH=CH—COO—, P is acrylate or methacrylate, R is halogen, cyano or an optionally fluorinated achiral or chiral alkyl or alkoxy group with 1 to 15 C atoms, n is 0, n is 1 and Sp is alkylene with 1 to 15, in particular 1 to 7, C atoms.

If R in formula I is an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, methoxy, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2- (=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

In the compounds of formula I R may be an achiral or a chiral group. In case of a chiral group they are preferably selected according to the following formula III:

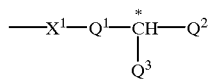

III wherein
$X^1$ is —O—, —CO—, —COO—, —OCO—, —OCOO— or a single bond,
$Q^1$ is an alkylene or alkylene-oxy group with 1 to 10 C atoms or a single bond, in which the oxy group is preferably adjacent to the chiral C atom adjacent to Q',
$Q^2$ is an alkyl or alkoxy group with 1 to 10 C atoms which may be unsubstituted, mono- or polysubstituted by halogen or CN, it being also possible for one or more non-adjacent $CH_2$ groups to be replaced, in each case independently from one another, by —O—, —S—, —NH—, —N($CH_3$)—, —CO—, —COO—, —OCO—, —OCO—O—, —S—CO— or —CO—S— in such a manner that oxygen atoms are not linked directly to one another,
$Q^3$ is halogen, a cyano group or an alkyl or alkoxy group with 1 to 4 C atoms different from $Q^2$.

Preferred chiral groups R are 2-butyl (=1-methylpropyl), 2-methylbutyl, 2-methylpentyl, 3-methylpentyl, 2-ethylhexyl, 2-propylpentyl, 2-octyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy for example.

In addition, compounds of formula I containing an achiral branched group R may occasionally be of importance, for example, due to a reduction in the tendency towards crystallization. Branched groups of this type generally do not contain more than one chain branch. Preferred achiral branched groups are isopropyl, isobutyl (=methylpropyl), isopentyl (=3-methylbutyl), isopropoxy, 2-methylpropoxy and 3-methylbutoxy.

Very preferably R in formula I is halogen, cyano or an optionally fluorinated achiral or chiral alkyl or alkoxy group with 1 to 15 C atoms.

Another preferred embodiment of the present invention relates to compounds of formula I wherein R is P—(Sp—X)$_n$—.

P in formula I is preferably an acrylate group, a methacrylate group, a vinyl or vinyloxy group, an epoxy group, a styrene group or a propenyl ether group, especially preferably an acrylate, methacrylate vinyl or vinyloxy group.

As for the spacer group Sp in formula I all groups can be used that are known for this purpose to the skilled in the art. The spacer group Sp is preferably a linear or branched alkylene group having 1 to 25 C atoms, in particular 1 to 12 C atoms, in which, in addition, one or more non-adjacent $CH_2$ groups may be replaced by —O—, —S—, —NH—, —N($CH_3$)—, —CO—, —O—CO—, —S—CO—, —O—COO—, —CO—S—, —CO—O—, —CH (halogen)— or —CH(CN)—.

Typical spacer groups are for example —($CH_2$)$_o$—, —($CH_2CH_2O$)$_p$—$CH_2CH_2$—, —$CH_2CH_2$—S—$CH_2CH_2$— or —$CH_2CH_2$—NH—$CH_2CH_2$—, with o being an integer from 2 to 12 and p being an integer from 1 to 3.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene for example.

Especially preferred are inventive compounds of formula I wherein Sp is an alkyl or alkoxy group with 2 to 6 C atoms. Straight-chain alkyl or alkoxy groups are especially preferred.

In another preferred embodiment of the invention the chiral compounds of formula I comprise at least one spacer group Sp that is a chiral group of the formula IV:

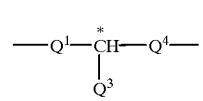

IV wherein
$Q^1$ and $Q^3$ have the meanings given in formula III, and
$Q^4$ is an alkylene or alkylene-oxy group with 1 to 10 C atoms or a single bond, being different from $Q^1$.

In the event that R is P—Sp—X—, the two spacer groups Sp in the compounds of formula I may be identical or different.

Of the preferred compounds described above particularly preferred are those wherein n is 1.

Further preferred are compounds comprising both a group P—(Sp—X)$_n$— wherein n is 0 and a group P—(Sp—X)$_n$— wherein n is 1.

The inventive compounds of formula I can be synthesized according to or in analogy to methods which are known per se and which are described in standard works of organic chemistry such as, for example, Houben-Weyl, Methoden der organischen Chemie, Thieme-Verlag, Stuttgart. Some specific methods of preparation can be taken from the examples.

Furthermore, inventive compounds can be prepared according to or in analogy to the following reaction schemes, starting from the phenols of formula I*. The synthesis of the phenols of formula I* is described in the International Application WO 91-03450, the entire disclosure of which is incorporated into this application by way of reference.

Scheme 1

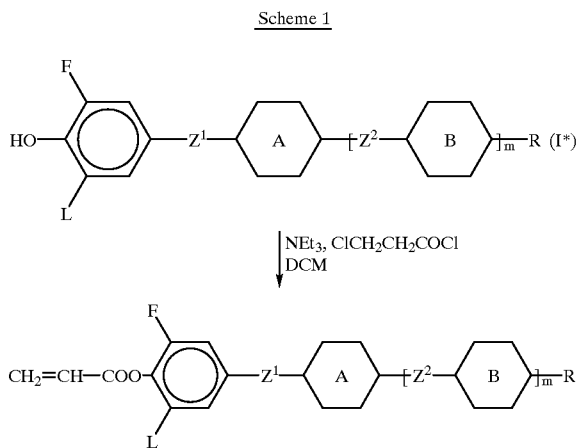

Other polymerizable mesogenic compounds that can be used as comonomers together with the inventive compounds for the preparation of polymers or polymer films are disclosed for example in WO 93/22397; EP 0,261,712; DE 195,04,224; WO 95/22586 or WO 97/00600. The compounds disclosed in these documents, however, are to be regarded merely as examples that shall not limit the scope of this invention.

Typical examples representing such polymerizable mesogenic compounds are shown in the following list of compounds, which should, however, be taken only as illustrative and is in no way intended to restrict, but instead to explain the present invention:

wherein L, $Z^1$, $Z^2$, A, B, m and R have the meaning of formula I and q is an integer from 1 to 15.

Scheme 2

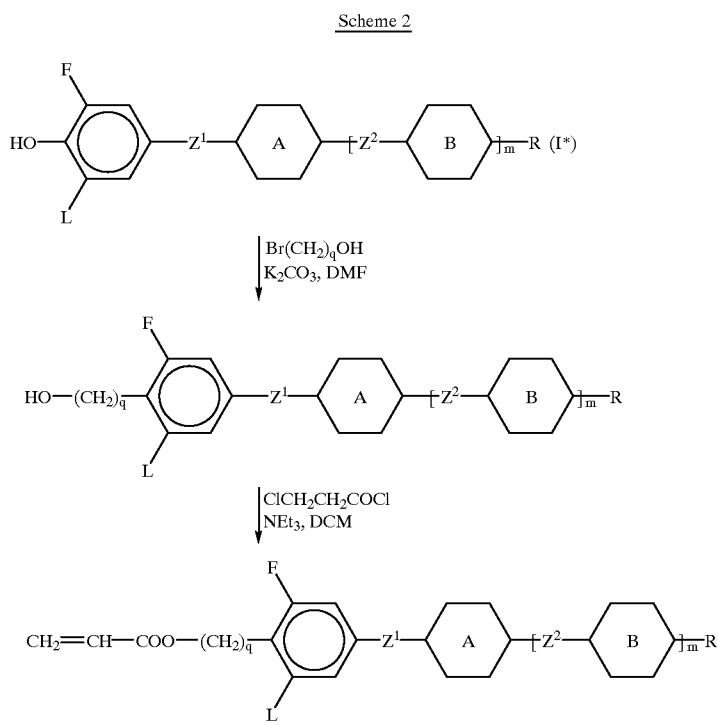

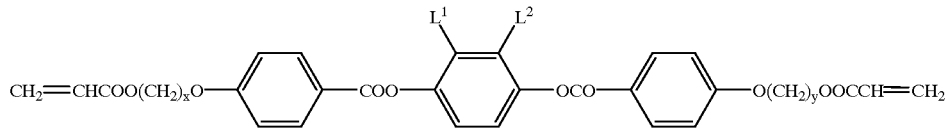
(V1)
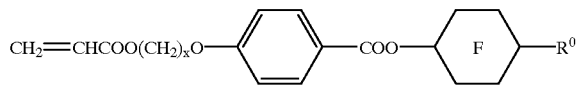
(V2)
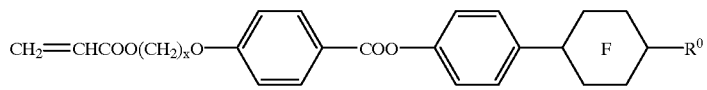
(V3)
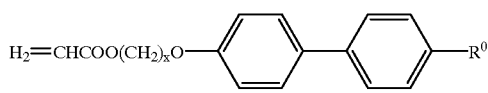
(V4)
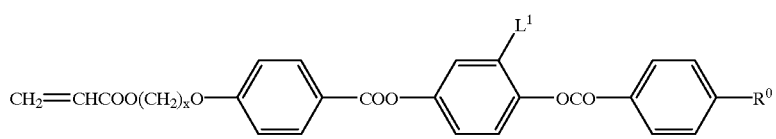
(V5)
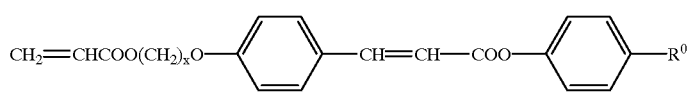
(V6)
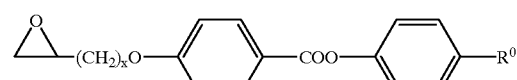
(V7)
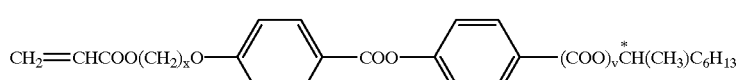
(V8)
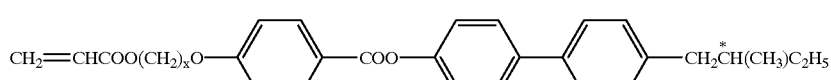
(V9)
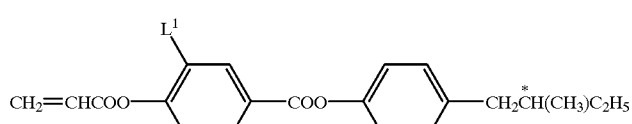
(V10)
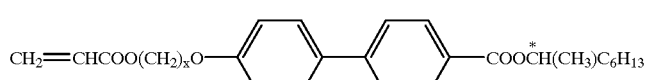
(V11)
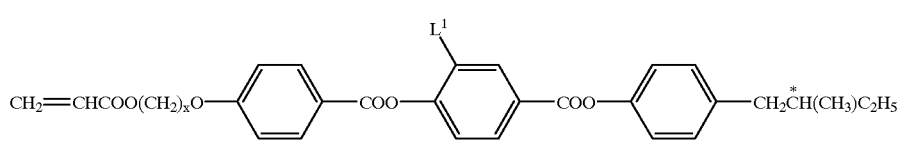
(V12)

-continued

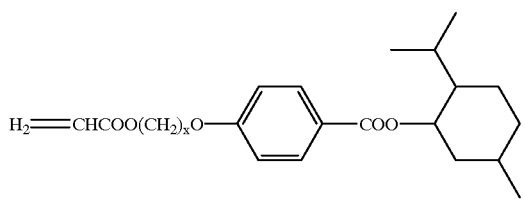
(V13)

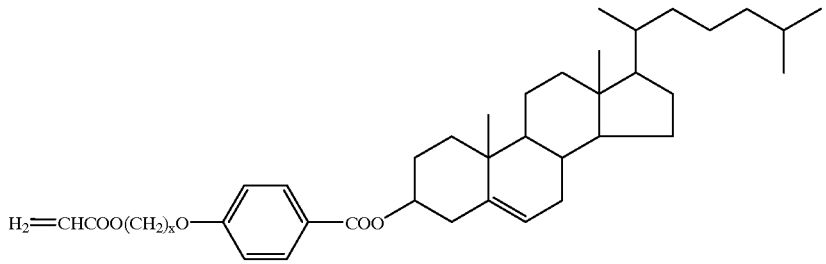
(V14)

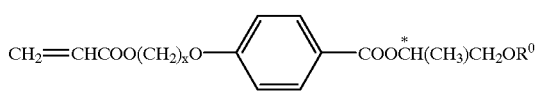
(V15)

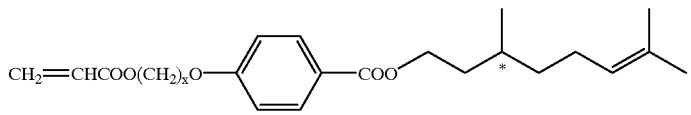
(V16)

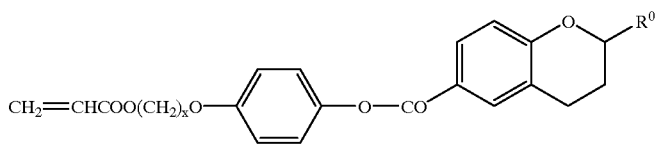
(V17)

In these compounds x and y are each independently 1 to 12 F is a 1,4-phenylene or 1,4-cyclohexylene group, $R^0$ is halogen, cyano or an optionally halogenated alkyl or alkoxy group with 1 to 12 C atoms and $L^1$ and $L^2$ are each independently H, F, Cl, CN, or an optionally halogenated alkyl, alkoxy or alkanoyl group with 1 to 7 C atoms.

The polymerizable mesogenic compounds of formula I can be mono- or bifunctional, i.e. they can comprise one or two polymerizable functional groups.

In a preferred embodiment of the invention the polymerizable liquid crystalline composition comprises at least one monofunctional and at least one bifunctional compound of formula I.

In another preferred embodiment of the present invention the polymerizable liquid crystalline composition comprises at least one two monofunctional compounds of formula I.

The polymerizable mesogenic compounds of formula I may also further comprise one or more chiral groups. Inventive compounds of formula I with a chiral group can be used e.g. for the prepration of thermochromic liquid crystalline mixtures or as chiral dopants.

In a preferred embodiment of the present invention the polymerizable liquid crystalline composition comprises at least one chiral polymerizable compound.

In another preferred embodiment the polymerizable liquid crystalline composition comprises at least one polymerizable chiral compound of formula I with one polymerizable group.

In another preferred embodiment the polymerizable liquid crystalline composition comprises at least one polymerizable chiral compound of formula I with two polymerizable groups.

It is also possible for the inventive composition to comprise one or more non-polymerizable chiral compounds, which may be mesogenic or non-mesogenic, in addition or alternatively to the chiral polymerizable compounds. For example, commercially available dopants, like e.g. R 811 or R 1011 (from Merck KGaA, Germany) can be used for this purpose.

Polymerizable mesogenic compositions are preferred that comprise 1 to 6, preferably 1 to 3 compounds of formula I.

In a preferred embodiment of the present invention the polymerizable liquid crystalline composition comprises 1 to 80% by weight, preferably 2 to 60%, in particular 5 to 40% by weight of one or more compounds of formula I.

In the polymerizable compositions comprising monofunctional compounds of formula I, the concentration of each of these compounds is preferably 1 to 60%, in particular 2 to 45%, very preferably 3 to 35% by weight of the total mixture.

In the polymerizable compositions comprising bifunctional compounds of formula I, the concentration of each of these compounds is preferably 1 to 50%, in particular 2 to 35%, very preferably 3 to 25% by weight of the total mixture.

The inventive polymerizable liquid crystalline compositions can additionally comprise one or more other suitable components, such as, for example, catalysts, sensitizers, stabilizers, co-reacting monomers or surface-active compounds.

It is also possible, in order to increase crosslinking of the polymers, to add up to 20% of a non mesogenic compound with two or more polymerizable functional groups to the polymerizable composition alternatively or additionally to the multifunctional polymerizable mesogenic compounds.

Typical examples for difunctional non mesogenic monomers are alkyldiacrylates or alkyldimethacrylates with alkyl groups of 1 to 20 C atoms. Typical examples for non mesogenic monomers with more than two polymerizable groups are trimethylpropanetrimethacrylate or pentaerythritoltetraacrylate.

Liquid crystalline polymers can be obtained from the inventive polymerizable compounds and compositions e.g. by solution polymerization or by in-situ polymerization.

For example, solution polymerization can be carried out in a solvent like dichloromethane, tetrahydrofuran or toluene using AIBN as an initiator and heating for 24 hours at 30 to 60° C.

The in-situ polymerization of polymerizable liquid crystalline compounds is described in detail by D. J.Broer et al., Makromol.Chem. 190, 2255ff. and 3202ff. (1989).

The polymerizable liquid crystal compounds and compositions according to this invention are preferably polymerized in situ as described in the foregoing and the following.

The inventive compounds and polymerizable liquid crystalline compositions are particularly useful for the preparation of anisotropic polymer films, such as nematic or cholesteric polymer films, with uniform molecular orientation.

Thus, another object of the invention is an anisotropic polymer film with an oriented liquid crystalline phase that is obtainable by polymerizing a polymerizable liquid crystalline composition comprising at least one polymerizable mesogenic compound of formula I.

To prepare an anisotropic polymer film with uniform orientation, an inventive polymerizable mesogenic composition is preferably coated onto a substrate, aligned and polymerized in situ by exposing them to heat or actinic radiation. Alignment and curing are preferably carried out in the liquid crystalline phase of the composition.

Actinic radiation means irradiation with light, like UV light, IR light or visible light, irradiation with X-rays or gamma rays or irradiation with high energy particles, such as ions or electrons. As a source for actinic radiation for example a single UV lamp or a set of UV lamps can be used. Another possible source for actinic radiation is a laser, like e.g. a UV laser, an IR laser or a visible laser.

When polymerizing by means of UV light, for example a photoinitiator can be used that decomposes under UV irradiation to produce free radicals or ions that start the polymerization reaction.

It is also possible to use a cationic photoinitiator, when curing reactive mesogens with for example vinyl and epoxide reactive groups, that photocures with cations instead of free radicals.

As a photoinitiator for radical polymerization for example the commercially available Irgacure 651, Irgacure 184, Darocure 1173 or Darocure 4205 (all from Ciba Geigy AG) can be used, whereas in case of cationic photopolymerization the commercially available UVI 6974 (Union Carbide) can be used.

Preferably the polymerizable liquid crystalline composition comprises 0.01 to 10%, in particular 0.05 to 8%, very preferably 0.1 to 5% by weight of a photoinitiator, especially preferably a UV-photoinitiator.

In a preferred embodiment of the invention the polymerization of the polymerizable mesogenic composition is carried out under an atmosphere of inert gas, preferably under a nitrogen atmosphere.

As a substrate for example a glass or quarz sheet as well as a plastic film or sheet can be used. It is also possible to put a second substrate on top of the coated mixture prior to, during and/or after polymerization. The substrates can be removed after polymerization or not. When using two substrates in case of curing by actinic radiation, at least one substrate has to be transmissive for the actinic radiation used for the polymerization.

Isotropic or birefringent substrates can be used. In case the substrate is not removed from the polymerized film after polymerization, preferably isotropic substrates are used.

Preferably at least one substrate is a plastic substrate such as for example a film of polyester such as polyethyleneterephthalate (PET), of polyvinylalcohol (PVA), polycarbonate (PC) or triacetylcellulose (TAC), especially preferably a PET film or a TAC film. As a birefringent substrate for example an uniaxially stretched plastic film can be used. For example PET films are commercially available from ICI Corp. under the trade name Melinex.

In a preferred embodiment of the present invention, the inventive polymerizable mesogenic composition is coated as a thin layer on a substrate or between substrates and is aligned in its liquid crystal phase to give a uniform orientation.

A uniform orientation can be achieved for example by shearing the mixture, e.g. by means of a doctor blade. It is also possible to apply an alignment layer, for example a layer of rubbed polyimide or sputtered $SiO_x$, on top of at least one of the substrates. In some cases, the mixtures orient themselves spontaneously on the substrate, or good alignment is achieved already by the act of coating the mixture.

In another preferred embodiment, a second substrate is put on top of the coated material. In this case, the shearing caused by putting together the two substrates is sufficient to give good alignment.

It is also possible to apply an electric or magnetic field to align the coated mixture.

In some cases it is of advantage to apply a second substrate not only to aid alignment of the polymerizable mixture but also to exclude oxygen that may inhibit the polymerization. Alternatively the curing can be carried out under an atmosphere of inert gas. However, curing in air is also possible using suitable photoinitiators and high lamp power. When using a cationic photoinitiator oxygen exclusion most often is not needed, but water should be excluded.

For the preparation of anisotropic polymer gels, the polymerizable mesogenic compound can be polymerized in situ as described above, however, in this case alignment of the polymerizable mixture is not necessarily required, although it may be desired for specific applications.

The invention also relates to the use of inventive compounds, compositions and polymers in liquid crystal displays, such as STN, TN, AMD-TN, temperature compensation, guest-host, phase change or surface stabilized or polymer stabilized cholesteric texture (SSCT, PSCT) displays, in active and passive optical elements like polarizers, compensators, alignment layers, color filters or holographic elements, in adhesives, synthetic resins with anisotropic mechanical properties, cosmetics, diagnostics, liquid crystal pigments, for decorative and security applications, in nonlinear optics, optical information storage or as chiral dopants.

The inventive compounds of formula I are particularly suitable, and preferably used, for the preparation of oriented birefringent polymer layers or films that are used as alignment or compensation layers in liquid crystal displays, in particular where these layers are applied to the surface of the electrodes of the liquid crystal cell facing the liquid crystal mixture, i.e. inside the cell. They are in particular suitable for the preparation of retardation or compensation layers in black and white or color reflective TN displays, especially single polarizer reflective displays (SPRD), as described e.g. by M. Tillin, SID 1998 Digest, 311–314 and the references cited therein.

By using the inventive polymerizable compounds for birefringent optical polymer films in liquid crystal displays, it is possible to adapt the optical properties of the birefringent polymer, like e.g. the retardation or the dispersion, to those of the LC mixture, and thereby to optimize the electrooptical properties of the display.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius, and, unless otherwise indicated, all parts and percentages are by weight.

The entire disclosure of all applications, patents and publications, cited above, and of corresponding European application No. 98113151.9, Jul. 15, 1998 is hereby incorporated by reference.

The following abbreviations are used to illustrate the liquid crystalline phase behavior of the compounds: K=crystalline; N=nematic; S=smectic; Ch=cholesteric; I=isotropic. The numbers between these symbols indicate the phase transition temperatures in degree Celsius. Furthermore, the following abbreviations are used:

| DMF | Dimethyl formamide |
| DCM | Dichloromethane |
| $T_{N-I}$ | nematic - isotropic phase transition temperature |

EXAMPLES

Example 1

Compound (1a) was prepared from the phenol (1a*) as follows

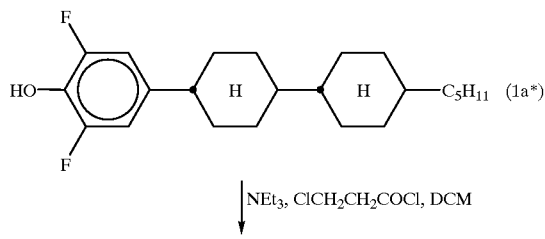

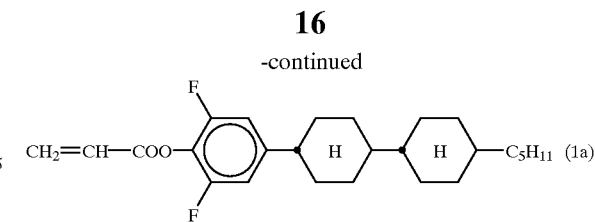

The phenol (1a*) can be prepared as described in the WO 91-03450.

5.44 g (14.9 mmol) of the phenol (1a*), 6.2 ml (44.7 mmol, 3 equivalents) triethylamine and 1.4 ml (14.9 mmol) 3-chloropropionyl chloride were stirred in 60 ml DCM at 35° C. for three days. The mixture was allowed to cool to room temperature, the solution was washed with water, dried over $Na_2SO_4$ and evaporated to dryness, leaving a residual brown solid. Purification was achieved using flash chromatography with DCM as eluant, to give upon evaporation of the appropriate fractions compound (1a) as a white solid (yield 3.7 g, 59%).

Compound (1a) exhibits a broad nematic phase, with the phase behavior K 85 N 220 I, and a low birefringence Δn of 0.109.

Compound (1b) was obtained analoguously from the corresponding phenol (1b*):

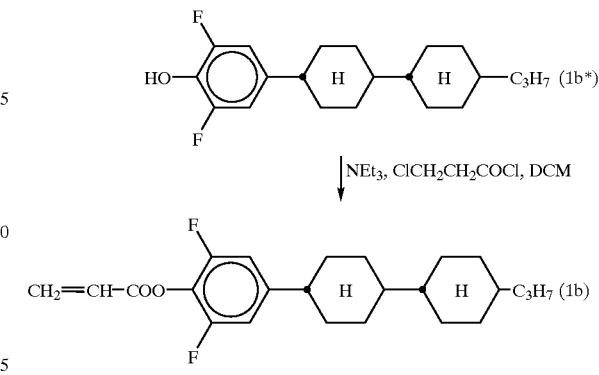

Compound (1b) exhibits a broad nematic phase, with the phase behavior K 110 N 200 I, and a low birefringence Δn of 0.106.

Δn of compounds (1a) and (1b) was determined in the nematic host mixture ZLI-3086 (commercially available from Merck KGaA, Darmstadt, Germany) at a concentration of 5.71 and 6.37% by weight respectively.

Example 2

Compound (2) was prepared as follows

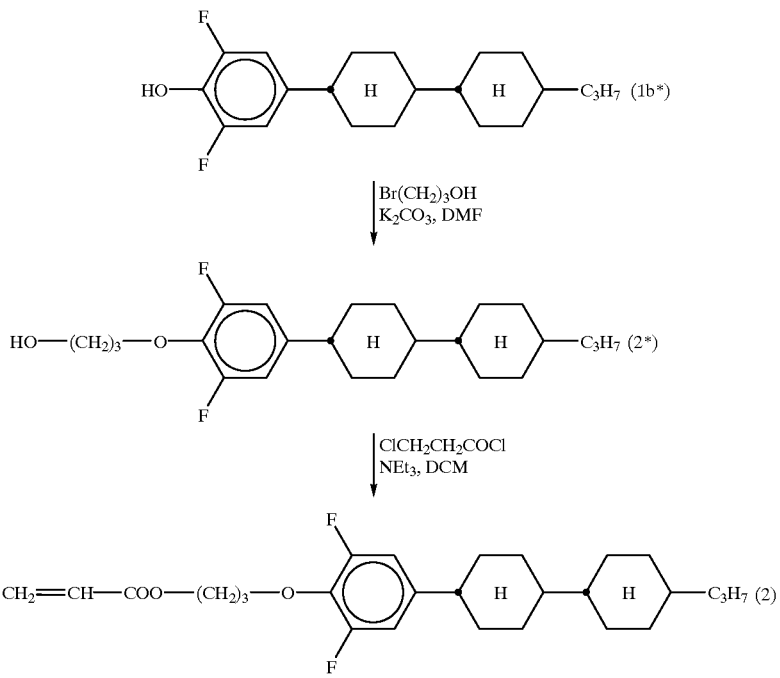

2a) 5.0 g (14.9 mmol) of phenol (1b*), 2.07 g (14.9 mmol) 3-bromopropanol and 2.88 g (20.9 mmol, 1.4 equivalent) potassium carbonate were stirred at 70° C. in dimethyl formamide for 60 hours. The mixture was allowed to cool to room temperature and was evaporated to dryness. The residue was dissolved in DCM, washed with water (3×200 ml), dried over $Na_2SO_4$ and evaporated to dryness on a rotatory evaporator. Purification was achieved by flash chromatography with petrol/ethyl acetate (4:1) as eluant to leave compound (2*) as a white solid (yield 1.82 g, 31%) with a melting point of 109° C.

2b) 1.8 g (4.3 mmol) of compound (2*), 2.4 ml (17.2 mmol, 4 equivalents) triethylamine and 0.45 ml (4.74 mmol, 1.1 equivalents) chloropropionyl chloride were stirred in 150 ml DCM for three days. The solution was allowed to cool to room temperature, washed with water (2×150 ml) and dried over $Na_2SO_4$, then evaporated to dryness on a rotatory evaporator. Purification was achieved by flash chromatography with petrol/DCM 1:1 as eluant to give upon evaporation of the appropriate fractions compound (2) as a white solid (yield 1.46 g, 76%). $^1$H-NMR showed the expected signals.

Compound (2) exhibits a broad nematic phase and a low melting point, with the phase behavior K 41 N 194 I, and a low birefringence Δn of 0.07.

Δn of compound (2) was determined in the nematic host mixture ZLI-3086 (commercially available from Merck KGaA, Darmstadt, Germany) at a concentration of 7.47% by weight.

The following compounds were prepared analoguously

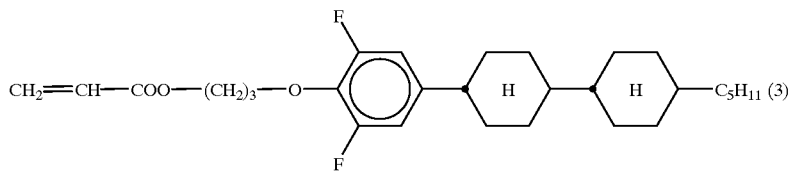

K 39.6 N 140.0 I, Δn=0.07

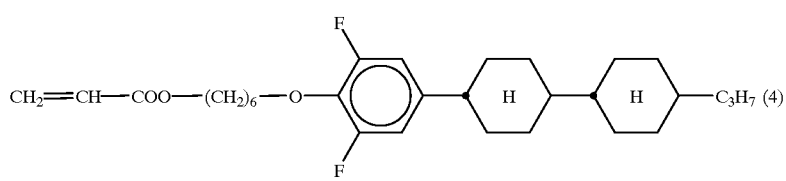

K 35.2 N 109.7 I, Δn=0.06

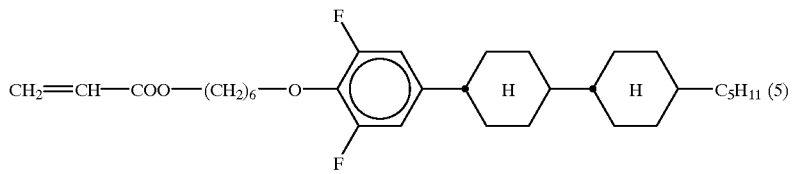

K 30.1 N 90 (polymerized), Δn=0.08

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various conditions and usages.

What is claimed is:

1. A polymerizable mesogenic fluorophenylene of formula I

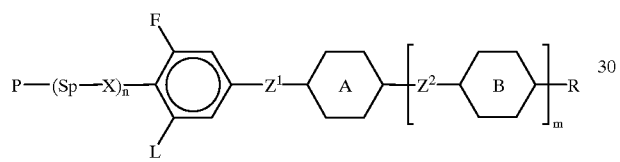

I wherein

P is CH$_2$=CW—COO—, WCH=CH—O—,

or CH$_2$=CH-Phenyl-(O)$_k$—

W is H, CH$_3$ or Cl, and k is 0 or 1,

Sp is a spacer group having 1 to 25 C atoms,

X is —O—, —S—, —CO—, —COO—, —OCO—, —CO—NH—, —NH—CO—, —CH$_2$CH$_2$—, —OCH$_2$—, —CH$_2$O—, —SCH$_2$—, —CH$_2$S—, —CH=CH—, —CH=CH—COO—, —OCO—CH=CH—, —C≡C—, or a single bond, n is 0 or 1, L is H or F, Z$^1$ and Z$^2$ are each independently —COO—, —OCO—, —CH$_2$CH$_2$—, —OCH$_2$—, —CH$_2$O—, —OCH$_2$—O— or a single bond, A and B are each independently

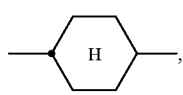

L$^1$ and L$^2$ are H or F, m is 0, 1 or 2, and

R is H, CN, halogen or a straight-chain or branched alkyl radical with up to 25 C atoms which is optionally mono- or polysubstituted by halogen or CN, and wherein in R one or more non-adjacent CH$_2$ groups are optionally replaced, in each case independently from one another, by —O—, —S—, —NH—, —N(CH$_3$)—, —CO—, —COO—, —OCO—, —OCO—O—, —S—CO—, —CO—S— or —C≡C— in such a manner that oxygen atoms are not linked directly to one another, or R is P—(Sp—X)$_n$—.

2. A polymerizable mesogenic fluorophenylene according to claim 1, of the following formulae

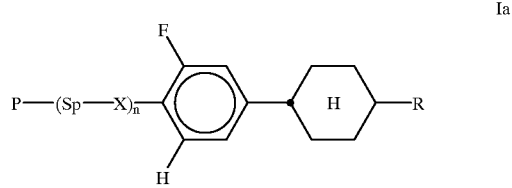

Ia

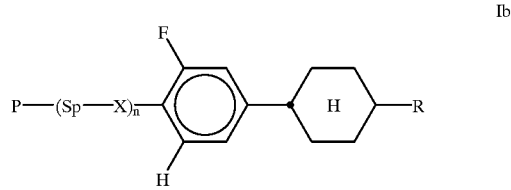

Ib

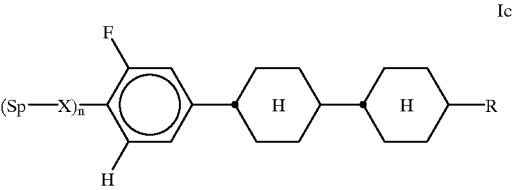

Ic

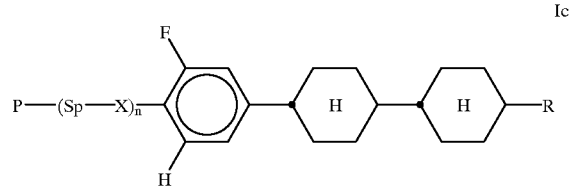

Id

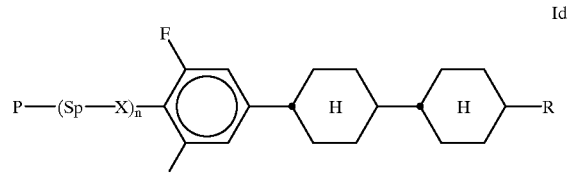

Ie

-continued

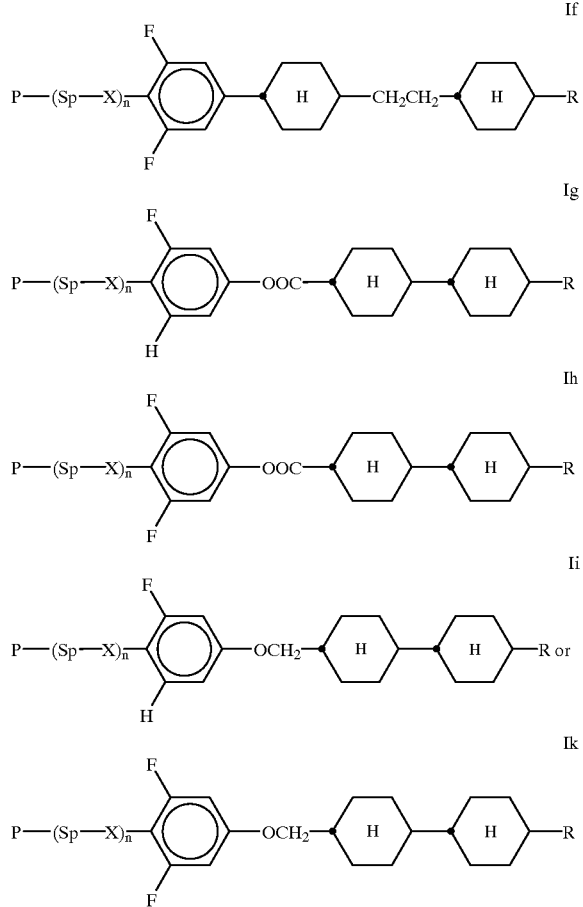

3. A polymerizable mesogenic fluorophenylene according to claim 1 wherein n is 0.

4. A polymerizable mesogenic fluorophenylene according to claim 1, wherein n is 1 and Sp is alkylene with 1 to 15 C atoms.

5. A polymerizable mesogenic fluorophenylene according to claim 1, wherein R is halogen, CN or achiral or chiral optionally fluorinated $C_{1-5}$-alkyl or $C_{1-15}$-alkoxy.

6. A polymerizable mesogenic fluorophenylene according to claim 1, wherein R is $P-(Sp-X)_n-$.

7. A liquid-crystalline composition comprising at least two polymerizable mesogenic compounds, wherein at least one compound is a compound according to claim 1.

8. A liquid-crystalline composition according to claim 7, comprising at least one polymerizable mesogenic compound having two polymerizable terminal groups.

9. A linear or crosslinked (co)polymer obtainable by (co)polymerization of a polymerizable mesogenic compound according to claim 1.

10. A linear or crosslinked (co)polymer obtainable by (co)polymerization of a polymerizable mesogenic compound according to claim 7.

11. A liquid crystal display which is a STN, TN, AMD-TN, temperature compensation, guest-host, reflective, phase change or surface or polymer stabilized cholesteric texture display, comprising a polymerizable mesogenic compound, wherein the compound is one according to claim 1.

12. An active or passive optical element which is a polarizer, compensator, alignment layer, color filter or holographic element, comprising a polymerizable mesogenic compound wherein the compound is one according to claim 1.

13. An adhesive, synthetic resin, cosmetic, diagnostic, liquid crystal pigment, nonlinear optic, optical information storage media or chiral dopant, with anisotropic mechanical properties comprising a polymerizable mesogenic compound, wherein the compound is one according to claim 1.

14. A process for the preparation of a polymer, comprising polymerizing a compound according to claim 1.

15. A process for the preparation of a polymer, comprising polymerizing a composition according to claim 7.

16. An electrooptical device comprising a liquid crystalline composition, wherien the composition is one according to claim 7.

* * * * *

UNITED STATES PATENT AND TRADEMARK OFFICE
CERTIFICATE OF CORRECTION

PATENT NO. : 6,183,822 B1
DATED : February 6, 2001
INVENTOR(S) : Farrand et al.

It is certified that error appears in the above-identified patent and that said Letters Patent is hereby corrected as shown below:

Column 19,
Line 58, delete "each independently".
Line 65, delete "$L^1$ and $L^2$ are H or F,".

Signed and Sealed this

Nineteenth Day of August, 2003

JAMES E. ROGAN
*Director of the United States Patent and Trademark Office*